United States Patent [19]
Davies

[11] Patent Number: 5,906,944
[45] Date of Patent: May 25, 1999

[54] PRENATAL SCREENING FOR FETAL ABNORMALITIES

[75] Inventor: Christopher John Davies, Energlyn Park, United Kingdom

[73] Assignee: Ortho-Clinical Diagnostics, Amersham, United Kingdom

[21] Appl. No.: 08/822,441

[22] Filed: Mar. 21, 1997

[30] Foreign Application Priority Data

Mar. 25, 1996 [GB] United Kingdom .................... 9606261

[51] Int. Cl.⁶ ................................................... G01N 33/48
[52] U.S. Cl. ............................... 436/65; 436/63; 422/68.1
[58] Field of Search ............................... 436/63, 65, 174, 436/906, 510; 422/68.1; 435/2, 806

[56] References Cited

U.S. PATENT DOCUMENTS

| | | | |
|---|---|---|---|
| 4,454,232 | 6/1984 | Breglio | 436/504 |
| 4,874,693 | 10/1989 | Bogart | 435/7.92 |
| 5,100,806 | 3/1992 | Macri | 436/518 |
| 5,252,489 | 10/1993 | Macri | 436/87 |
| 5,258,907 | 11/1993 | Macri | 436/510 X |
| 5,316,953 | 5/1994 | Macri | 436/87 |
| 5,324,667 | 6/1994 | Macri | 436/518 |
| 5,324,668 | 6/1994 | Macri | 436/518 |
| 5,506,150 | 4/1996 | Canick et al. | 436/510 |
| 5,605,843 | 2/1997 | Canick et al. | 436/510 |
| 5,716,853 | 2/1998 | Cuckle et al. | 436/510 |

FOREIGN PATENT DOCUMENTS

| | | |
|---|---|---|
| 0327377 A2 | 8/1989 | European Pat. Off. . |
| 617921 | 10/1994 | European Pat. Off. . |
| 635722 | 1/1995 | European Pat. Off. . |
| 701131 | 3/1996 | European Pat. Off. . |
| 87/05702 | 9/1987 | WIPO . |
| 89/00696 | 1/1989 | WIPO . |
| 90/08325 | 7/1990 | WIPO . |
| 94/12884 | 6/1994 | WIPO . |
| 94/21686 | 9/1994 | WIPO . |

OTHER PUBLICATIONS

Forest et al. "Screening for Down Syndrome . . . " *Clinical Biochemistry*, vol. 28, No. 4, pp. 443–449, 1995.
Spencer et al. "First Trimester Biochemical Screening . . . " *Annals of Clinical Biochemistry*, vol. 31, pp. 447–454, 1994.
N. Wald et al., "First Trimester Biochemical Screening for Down's Syndrome", Ann Med, 26, pp. 23–29, 1994.
T. Reynolds and M. Penney, "The Mathematical Basis of Multivariate Risk Screening: with Special Reference to Screening for Down's Syndrome Associated Pregnancy", Ann. Clin. Biochem. 27: pp. 452–458, 1989.
P. Bischof et al., "Amniotic Fluid and Plasma Concentrations of Pregnancy–Associated Plasma Protein–A (PAPP–A) throughout Pregnancy: Comparison with Other Fetoplacental Products", Brit J Obstet Gynaecol, 89: pp. 358–363, 1982.
H. Cuckle et al., "Estimating a Woman's Risk of Having a Pregnancy Associated with Down's Syndrome Using Her Age and Serum Alpha–Fetoprotein Level", Brit J Obstet Gynaecol, 94: pp. 387–402, 1987.

G. Lockwood et al., "A Sonographic Screening Method for Down Syndrome", Am J Obstet Gynecol, 157: pp. 803–808, 1987.
I. Stabile et al., "Measurement of Placental Decidual, and Fetal Proteins Before and After Chorionic Villus Samping: Prenatal Diagnosis," 8: pp. 387–391, 1988.
N. Wald et al., "Maternal Serum Unconjugated Oestriol as an Antenatal Screening Test for Down's Syndrome", Brit J Obstet Gynaecol, 95: pp. 334–341, 1988.
N. Wald et al., "Maternal Serum Screening for Down's Syndrome in Early Pregnancy", Brit Med J, 297: pp. 883–887, 1988.
T. Reynolds and R. John, "Comparison of Assay Kits for Unconjugated Estriol Shows That Expressing Results as Multiples of the Median Causes Unacceptable Variation in Calculated Risk Factors for Down Syndrome", Clin Chem 38: pp. 1888–1892, 1992.
T Reynolds et al., "Utility of Unconjugated Estriol in Screening for Down Syndrome is Not Proven", Clin Chem 39: pp. 2023–2025, 1993.
J. Crossley et al., "Prenatal Screening for Chromosome Abnormalities Using Maternal Serum Chorionic Gonadotrophin, Alpha–Fetoprotein, and Age", Prenatal Diagnosis, 11: pp. 83–101, 1991.
H. Cuckle, Measuring Unconjugated Estriol in Maternal Serum to Screen for Fetal Down Syndrome, Clin Chem, 38: No. 9, pp. 1687–1689, 1992.
P. Kratzer et al., "First Trimester Aneuploidy Screening Using Multiple Biochemical Serum Markers", Am J Hum Genet, 51 (4Supp4): A268 Abstr 1057, 1992.
D. Aitken et al., "PAPPA as a Marker of Trisomy 21 in the First Trimester", Clin Chem 39: p. 1170, Abstr 0236, 1993.
B. Brambati et al. Low Maternal Serum Levels of Pregnancy Associated Plasma Protein A (PAPP–A) in the First Trimester in Association with Abnormal Fetal Karyotype: Brit J Obstet Gynaecol, 100: pp. 324–326, 1993.
M. Macintosh et al., "Predicting Fetal Chromosome Anomalies in the First Trimester Using Pregnancy Associated Plasma Protein–A: A Comparison of Statistical Methods", Methods Inform Med, 32: pp. 175–179, 1993.
M. Macintosh and T. Chard, "Biochemical Screening for Down's Syndrome in the First Trimester of Pregnancy", Fetal Mat Med Rev, 5: pp. 181–190: 1993.
Y. Sorokin et al., "Postmortoem Chorionic Villus Sampling: Correlation of Cytogenetic and Ultrasound Findings", Am Jour of Med Genetics, 39: pp. 314–316, 1991.

*Primary Examiner*—Maureen M. Wallenhorst

[57] ABSTRACT

There is disclosed a method for antenatal screening for an abnormality in a fetus using a bodily fluid, the fluid containing a marker which at one stage of gestation (stage A) the mean or median level) of the marker differs by less than 20% between pregnancies which are affected and unaffected by the abnormality and at another stage of gestation (stage B) differs by more than 50% between such affected and unaffected pregnancies, there being a period of at least 3 weeks between Stage A and Stage B and an apparatus for carrying out the method.

9 Claims, 2 Drawing Sheets

PRENATAL SCREENING FOR FETAL ABNORMALITIES

BACKGROUND OF THE INVENTION

This invention relates to a method and apparatus for prenatal screening for fetal abnormalities.

The risk of many fetal abnormalities is known to be associated with advanced maternal age, and this factor has been used for many years as the basis for the selection of pregnant women at highest risk for further investigation. Further investigation involves the sampling of the amniotic fluid by amniocentesis in order to isolate fetal cells which may then be examined for chromosomal abnormalities by karyotyping. This is a procedure which is not completely free from risk to both mother and fetus. It is estimated that the risk of spontaneous miscarriage as a result of this procedure is of the order of 0.5% to 1.0%.

Other risk factors have been identified which may also be used in selecting those women at highest risk of fetal abnormality. For example Wald et al in European Patent No. 362294 B1 have described how maternal serum concentrations of alpha-fetoprotein (AFP), human chorionic gonadotrophin (hCG) and unconjugated estriol (UE3) taken in the second trimester of pregnancy (from 13 to 26 weeks) may be used to calculate an individual woman's risk of subsequently giving birth to a child with Down Syndrome. Macri in European Patent Specification No. 409956A has described how measurement of the free-beta subunit of hCG may also be used as a marker for fetal Down Syndrome. In our European Patent Specification No. 627032 we describe how the combination of the free beta hCG and pregnancy associated placental protein A (PAPP-A) may also be used to predict the risk of fetal abnormalities in the first trimester of pregnancy.

All maternal serum markers have been identified on the basis that the concentrations found in abnormal pregnancies differ from those in normal pregnancies. Current teaching dictates that substances found in maternal serum which do not show a difference in concentration between abnormal and normal pregnancies are not as useful as maternal serum markers. Some maternal serum markers are only of apparent use at certain stages of the pregnancy. For example PAPP-A concentrations are known to be lower in the first trimester of pregnancy where the fetus has Down Syndrome, yet show no difference in the second trimester of pregnancy. Conversely maternal serum hCG has been shown not to be a very effective marker for fetal Down Syndrome in the first trimester. Macintosh M.C.M & Chard T; Fetal. Mat. Med. Rev. 5 : 181–190, 1993—Wald N. J. Kennard A. & Smith D., Ann. Med., 26: 23–29, 1994. Current teaching therefore indicates that measurement of PAPP-A in the second trimester of pregnancy or hCG in the first trimester of pregnancy would be of no use in screening for fetal Down Syndrome.

It is desirable that methods of prenatal screening are developed in which a correction is possible to remove the influence of between subject variation.

SUMMARY OF THE INVENTION

According to the present invention we provide a method for antenatal screening for an abnormality in a fetus using bodily fluid such as a serum marker and/or a precursor or metabolite of said marker, the marker being one where at one stage of gestation (stage A) the mean or median level of the marker, corrected for gestational age if necessary, differs less than 20% between pregnancies which are affected and unaffected by the abnormality and at another stage of gestation (stage B) differs by more than 50% between such affected and unaffected pregnancies, there being a period of at least 3 weeks between Stage A and Stage B, characterised in that determinations of concentrations of the marker for an individual woman are made at stage A and at stage B and are compared to produce a normalised concentration and the thus determined normalised concentration is compared with similarly determined normalised concentrations for populations of women with and without said fetal abnormality.

Further according to the present invention we provide an apparatus comprising means adapted for receiving measurements of levels of a serum marker in a body fluid (particularly blood) of a pregnant woman and/or precursor or metabolite of said marker, the marker being one where at one stage of gestation (stage A) the mean or median level of the marker, corrected for gestational age if necessary, differs by less than 20% between pregnancies which are affected and unaffected by a fetal abnormality and at another stage of gestation (stage B) differs by more than 50% between such affected and unaffected pregnancies, there being a period of at least 3 weeks between Stage A and Stage B, and computer means for comparing the measurements of these levels with each other and to sets of reference data to determine fetal abnormalities characterised in that the computer means is capable of comparing concentrations of the marker for an individual woman made at stage A and at stage B to produce a normalised concentration and to compare the thus determined normalised concentration with reference data relating to similarly determined normalised concentrations for populations of women with and without said fetal abnormality.

The concentrations of most maternal serum markers change during pregnancy as a result of changes in the size and maturity of the fetus or placenta. In order to enable valid comparisons to be made between concentrations at different stages of pregnancy they must first be normalised by dividing the actual value by the median value found in the unaffected population of pregnant women at that gestational age (termed the Multiple of the Median or MoM). The median is usually used in preference to the mean to avoid the undue influence of outlying values.

None of these markers, either used individually or when combined statistically in a multivariate mathematical model, are diagnostic. The distributions of concentrations found in affected and unaffected groups show marked overlap, which does not permit the complete separation of the two groups.

The effectiveness of any maternal serum marker is therefore governed not only by the difference in mean value of the distributions of concentrations in affected and unaffected pregnancies but also by the variance around the mean. If the variance is small, then the population of abnormal pregnancies is better separated from the normal population than when the variance is large. A small variance is therefore a highly desirable characteristic of any screening test.

DETAILED DESCRIPTION OF THE INVENTION

Figure 1:
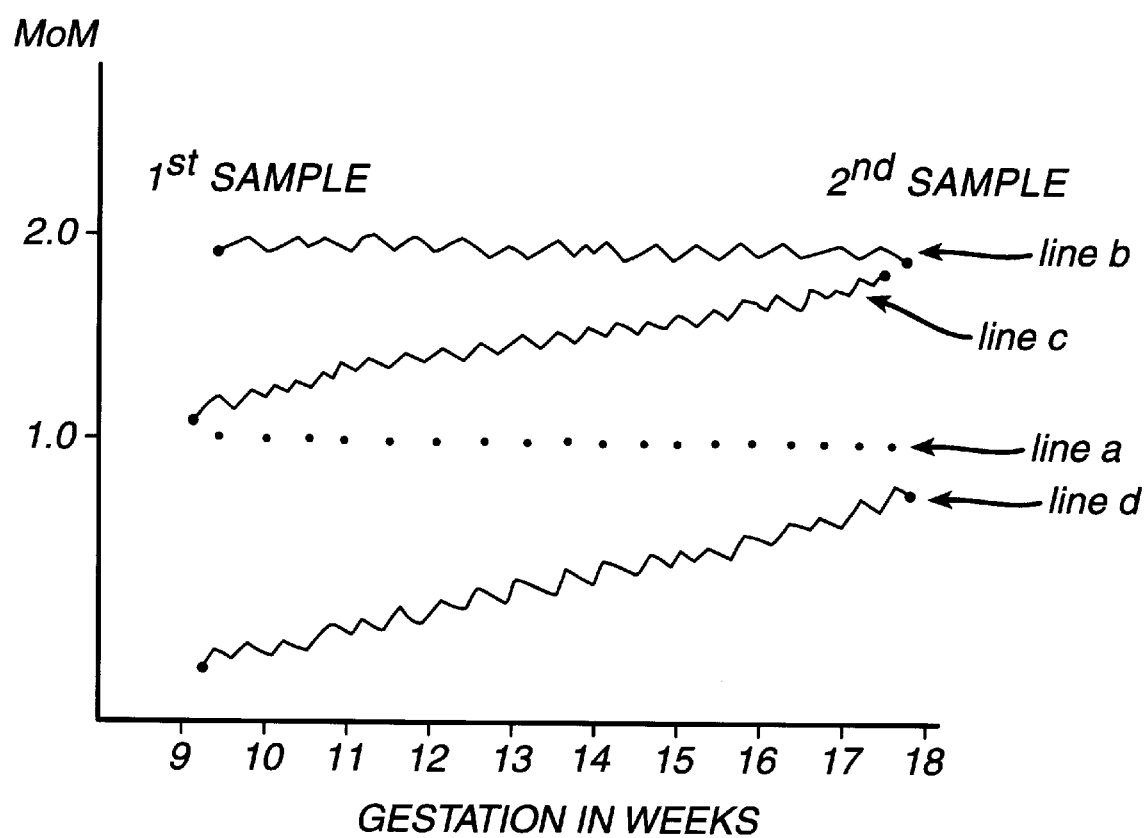
FIG. 1 is a graph of the median MoM against gestation age in weeks using hCG as a marker.

The observed variance of maternal serum marker concentrations is made up of two principal components:

1. The variation in concentration between different pregnant women; and
2. The variation within an individual woman from occasion to occasion.

If SDb represents the variation in concentration between pregnant women (expressed as the standard deviation) and SDi the variation within an individual woman from occasion to occasion (expressed as the standard deviation) then the observed total variation seen when examining a group of pregnant women is given by:

$$SDt = \sqrt{SDb^2 + SDi^2}$$

where SDt is the observed standard deviation for a population of pregnant women.

For any one individual woman, values obtained from occasion to occasion will vary only within the boundaries defined by the within subject variation centred around that individual woman's homeostatic set-point concentration. The homeostatic set point is the average value found in an individual woman around which day-to-day variation may be seen. The observed variation of the entire population will be much larger than the within-subject variation because of the additional variation caused by differences between women in the position of their individual homeostatic set-points.

If it were possible to remove the component of variation attributable to the between subject variation, the degree of separation of the distributions of maternal serum marker concentrations would increase leading to an increased ability of the test to discriminate between normal and abnormal pregnancies.

The present invention provides a correction to remove or reduce the influence of the between subject variation.

At different stages of gestation some maternal serum markers show no discriminatory ability between affected and unaffected pregnancies, in other words there is no or little difference in mean values between the groups.

Determination of the concentration of the maternal serum markers at such a stage of gestation provides an estimate of the homeostatic set-point for that individual woman (concentration A).

A sample is also taken when the maternal serum marker does not show good discrimination between affected and unaffected pregnancies (concentration B).

A comparison of the two concentrations A and B enables a normalised concentration (C) to be determined, for example simply by dividing B by A. The normalised concentration C for the entire population shows much less variation than is seen for the population distribution of concentration A or B, as the between-subject variation has now been eliminated by the normalised procedure.

In the method of the invention the concentration of the serum marker under consideration is determined at a time when it does not function effectively as a marker, i.e. at a time when it differs by less than 20% between affected and unaffected pregnancies. This determination will be referred to as value A. The concentration of the marker is also determined at a time when it does function effectively as a marker, i.e. at a time when it discriminates by more than 50% between affected and unaffected pregnancies. This determination will be referred to as value B.

The determinations of the marker to produce values A and B are separated in time by a period of at least 3 weeks, for example between 4 and 8 weeks. Preferably the determinations to produce values A and B are made in different trimesters of pregnancy for example the first sample could be taken at 8 weeks of gestation and the second sample at 16 weeks of gestation.

After their determinations values A and B are compared by any suitable method, preferably but not exclusively by division, to produce value C.

The determinations and comparison are done for an individual woman and the result is supplied to a computer equipped with an algorithm based upon figures for value C derived from measurements on a large number of women. Distribution curves for value C can be prepared and are sharper in outline and show less variation around the mean than distribution curves for other values thus giving greater separation between the distributions for unaffected pregnancies and for pregnancies affected by fetal abnormalities. Using the computer it is possible to ascertain how a C value determined for an individual woman compares with the value for a whole population i.e. with a general curve.

The invention may be applied using any marker which at one stage of gestation (stage A) discriminates by less than 20% between pregnancies which are affected and unaffected by the abnormality under consideration and at another stage (stage B) discriminates by more than 50% between such affected and unaffected pregnancies. In particular the invention is very suitably applied using intact hCG or the free alpha or beta subunits of hCG as the marker. Other suitable markers include AFP, PAPP-A, dimeric inhibin (inhibin A) and Schwangerschaft protein 1 (Pregnancy specific X-glycoprotein 1, SP1).

The method and apparatus of the invention are very suitable when the marker determined according to the invention is combined with measurements of one or more other markers, said other markers being measured either conventionally or, where appropriate, in accordance with the invention. Such other markers include dimeric inhibin, intact hCG, the free alpha or beta subunit of hCG, AFP, UE3, PAPP-A and Schwangerschaft protein 1.

The maternal body fluids on which measurements are made include for example, saliva, urine, amniotic fluid and particularly blood.

The method and apparatus of the invention can be used for antenatal screening for a wide range of pregnancy abnormalities. These include abnormalities such as ectopic pregnancy, neural tube defects, ventral wall defects and particularly fetal chromosomal abnormalities. The most significant and frequently occurring chromosomal abnormality is Down Syndrome (Trisomy 21). Other such abnormalities which may be screened for using the invention include Edwards Syndrome (Trisomy 18), Pateaus Syndrome (Trisomy 13), Turner Syndrome, Monosomy X and Kleinefelter's Syndrome. The invention may be used to screen for individual abnormalities or to screen for groups of abnormalities together, for example it could be used to screen for both Down Syndrome and Edwards Syndrome.

Measurements are carried out and analysed using the method of the invention on samples taken during an appropriate period of pregnancy. Preferably the measurements are made on samples taken in the first and second trimesters and often in the period between the beginning of the eighth week and the end of the second trimester. The woman's normalised serum value for the individual serum marker is divided by the normalised expected median value found in women with unaffected pregnancies at the same gestational age to derive the multiple of the median (MoM). The probability that the (MoM) values for the combination of serum markers tested belongs to the multivariate distribution of values found in unaffected pregnancies is calculated. The same calculation is performed by reference to the probability that the individual combination of values forms part of the multivariate distribution found in abnormal pregnancies. The ratio of the two probabilities is termed the likelihood ratio (LR) which indicates the likelihood that an individual woman has an affected pregnancy or not. The degree of separation between the multivariate distributions for affected and unaffected pregnancies changes with gestational age, i.e. there is a continuous change in the manner of calculating probability depending upon the gestational age. This continuous change can be built into the algorithm used in the calculation.

An individual woman has an a priori age related risk which is independent of the maternal serum marker concentrations. The woman's age related risk, by Baye's theorem, is modified by multiplying by the likelihood ratio (LR) obtained previously to derive a combined risk. This combined risk may then be used to counsel the woman regarding the relative risk of the abnormality as opposed to the risk of miscarriage associated with a subsequent diagnostic invasive procedure.

By way of example, in FIG. 1 the line (a) represents the median hCG MoM values for the unaffected population at different weeks of gestation ages expressed as MoM. By definition this is 1.0 MoM at all gestational ages. Line (b) refers to the concentration of hCG, expressed as MoM, for a woman with a normal pregnancy. The variation in value across the gestation is random, but centred on the homeostatic mean value of 2.0 MoM. If the second trimester sample (13 to 26 weeks) were the only one examined, then such a woman would be considered to be at high risk for fetal Down Syndrome on account of the high hCG concentration. Knowledge that the first sample is also high, at a stage of gestation where hCG is not an effective marker for Down Syndrome, indicates that the reason for the high hCG is due to a high homeostatic set-point rather than due to fetal Down Syndrome. Line (c) indicates the values for a woman with a Down Syndrome affected pregnancy who would correctly be identified as being high risk on the basis of a high hCG MoM in the second sample and a median homeostatic set-point in the first sample. In contrast line (d) represents a woman with a Down Syndrome affected pregnancy who would be considered at low risk for fetal Down Syndrome on the basis of the normal hCG result on the second sample only, but who would be considered high risk given the knowledge that the first sample revealed a very low homeostatic set-point.

One way of combining the results of the first and second sample is to divide the concentration when the marker is effective at discriminating the two populations by the concentration when it is not effective. In principle absolute effectiveness and absolute non-effectiveness of markers is not required, merely that the efficiency should be sufficiently different to enable normalisation to be effected around the homeostatic set-point for the individual woman.

EXAMPLE

By way of example Table 1 shows the mean and standard deviations (sd) of hCG Multiple of the normal population median, expressed as the natural logarithm [ln (MoM)], from a clinical trial involving 2765 women with unaffected pregnancies and 126 women where the fetus had Down Syndrome. All samples were taken between the 15th and 20th week of gestation.

TABLE 1

|  | Mean ln (MoM) | sd ln (MoM) |
| --- | --- | --- |
| Unaffected | 0.0000 | 0.5349 |
| Down Syndrome | 0.6934 | 0.5843 |

A further clinical trial was performed involving 170 women where samples were taken at a stage of pregnancy when hCG is not a marker for Down Syndrome, at 9–13 weeks completed gestation, and a further sample taken between 3 and 6 weeks later, at a period of gestation where hCG is known to be a marker for Down Syndrome, that is to say between 15 to 18 weeks gestation.

Each patient's second sample was normalised by the following equation:

hCG MoM for the second sample/HCG MoM for the first sample=normalised hCG MoM

Table 2 gives the mean and standard deviation of the ln (MoM) for the second sample before it has been normalised, and afterwards.

TABLE 2

|  | Mean ln (MoM) | Standard deviation |
| --- | --- | --- |
| ln (hCG MoM) second sample | 0.0000 | 0.5178 |
| normalised ln (hCG MoM) 2nd sample | 0.0000 | 0.3863 |

The variation is substantially reduced by the use of the first sample to normalise the second.

The between subject variance estimated from this group of 170 women with unaffected pregnancies, can be obtained by subtraction of the within-subject variance from the overall variance:

Between subject variance=$0.5178^2 - 0.3863^2 = 0.1189$

The between subject variance may be subtracted from the variance found in unaffected and Down Syndrome affected, the standard deviations of which are shown in Table 1, to give estimates of the between subject variance for unaffected and Down Syndrome affected pregnancies.

Variance in unaffected pregnancies=$0.5349^2 - 0.1189 = 0.16728$

Variance in Down Syndrome affected pregnancies=$0.5843^2 - 0.1189 = 0.22251$

Figure 2:
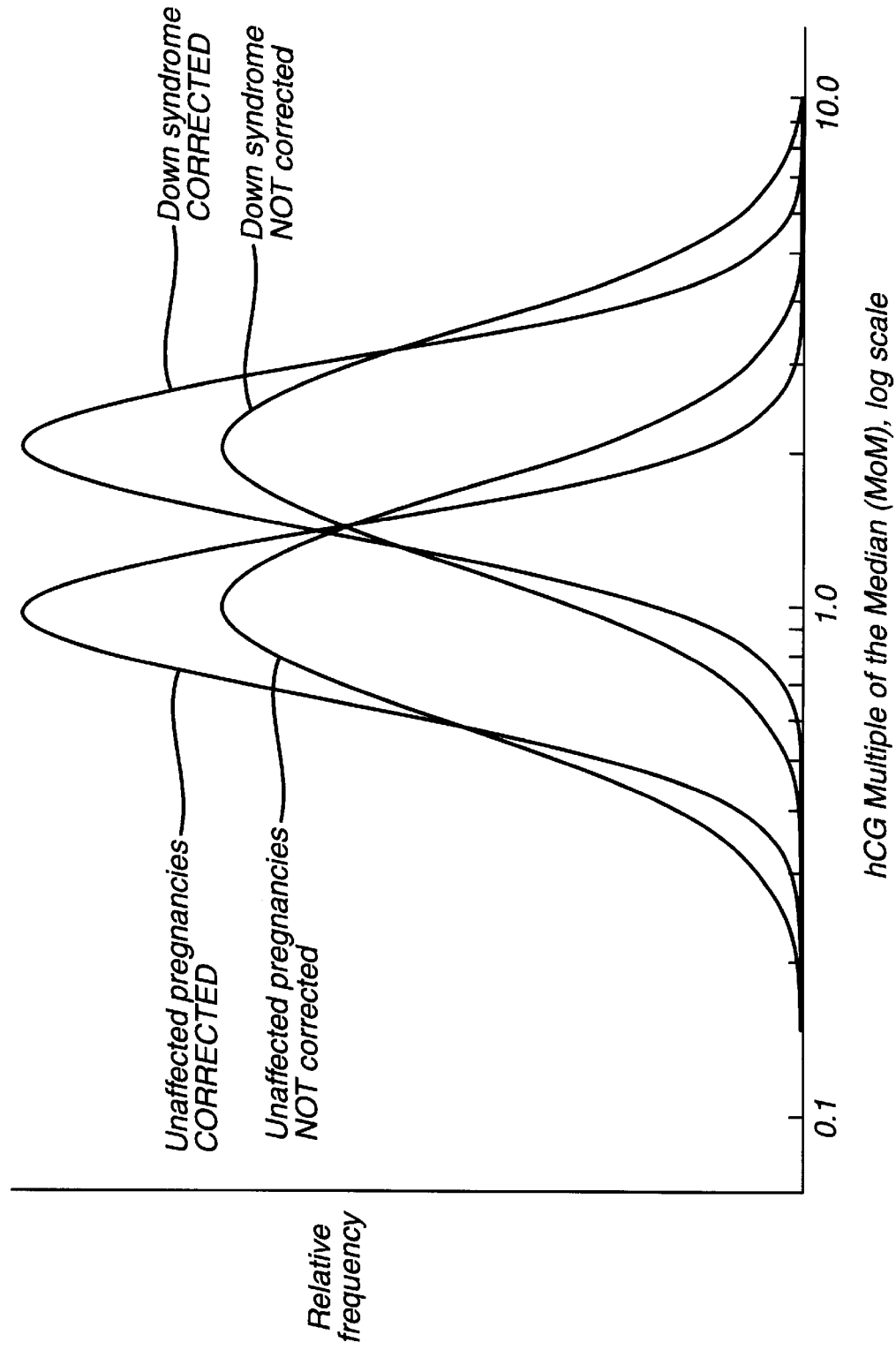
FIG. 2 is a graph which shows the reduction in overlap in the frequency distributions of hCG in pregnancies with and without correction for between subject variance according to the method of the invention.

The normalised standard deviations for unaffected and Down Syndrome affected pregnancies can be calculated from the variance normalised as above:

Standard deviation in unaffected pregnancies = $\sqrt{0.16728} = 0.4089$
Standard deviation in Down Syndrome affected pregnancies = $\sqrt{0.22251} = 0.4717$ The distribution of ln (hCG MoM) after normalisation for between subject variation now shows considerably less overlap between unaffected and Down Syndrome affected pregnancies. The reduction in overlap can be clearly seen in FIG. 2.

The benefit of this reduction in overlap between the affected and unaffected pregnancies, in terms of the effectiveness of the test in screening for fetal Down Syndrome can be derived from the two log Gaussian distributions for affected and unaffected pregnancies.

Table 3 shows the percentage of affected pregnancies (detection rate) and unaffected pregnancies (false-positive rate) higher than a range of normalised and for comparison, non-normalised, hCG MoM levels. For a screen positive rate of 2% the detection rate rises from 25% to 38%—non-normalised to normalised and the corresponding figures for a screen positive rate of 5% are 37% to 48%.

TABLE 3

| hCG MoM | Non-Normalised (%) | | Normalised for between subject variation (%) | |
|---|---|---|---|---|
| | detection rate | screen positive rate | detection rate | screen positive rate |
| 1.0 | 88 | 50 | 93 | 50 |
| 1.2 | 81 | 36 | 86 | 33 |
| 1.4 | 73 | 26 | 77 | 21 |
| 1.6 | 65 | 19 | 68 | 13 |
| 1.8 | 57 | 14 | 59 | 7 |
| 2.0 | 50 | 10 | 50 | 4 |
| 2.2 | 43 | 7 | 42 | 3 |
| 2.4 | 38 | 5 | 35 | 2 |
| 2.6 | 33 | 4 | 29 | 1 |
| 2.8 | 28 | 3 | 24 | 0.6 |
| 3.0 | 24 | 2 | 20 | 0.4 |

Table 3 clearly demonstrates the marked improvement in screening effectiveness using the invention.

In routine practice the normalised hCG MoM information would be combined with the prior odds due to maternal age. These procedures are well known to workers in the field.

In addition the information from the test could also be combined with other maternal serum markers for Down Syndrome either normalised for within subject variation or not.

This invention is not restricted to hCG but is of course available to other maternal serum markers which show a change in their discriminating ability at different stages of gestation, for example PAPP-A. Nor is there an absolute requirement for the marker to show a complete absence of discrimination at any stage of gestation. The same principles are applicable to those markers which show a decreased discrimination at a particular stage of gestation, such as Schwangerschaft protein 1 (Pregnancy specific X-glycoprotein 1, SP1) which has poor discriminatory ability in the second trimester but good discriminatory power in the first trimester.

The correction for between subject variation described in this example was simply achieved by dividing the hcG MoM value in the second trimester (when hcG is an effective marker for fetal Down Syndrome) by the hCG MoM value seen in the first trimester (when hCG is not a marker for fetal Down Syndrome).

Other methods of calculation to correct for between subject variation may be used, for example combining both tests together using a bivariate probability density function, as is currently done for the combination of different maternal serum markers (Reynolds and Penney, Annals of Clinical Biochemistry (1990), 27, 452–458, 1990).

I claim:

1. A method for antenatal screening for an abnormality in a fetus comprising obtaining a bodily fluid which at one stage of gestation (stage A) a mean or median level of a marker obtained from said bodily fluid differs by less than 20% between pregnancies which are affected and unaffected by the abnormality and at another stage of gestation (stage B) differs by more than 50% between such affected and unaffected pregnancies, there being a period of at least 3 weeks between stage A and stage B, determining a concentration value of the marker for an individual woman at stage A and at stage B, and comparing said concentration values to produce a normalized concentration value and comparing the thus determined normalised concentration value with similarly determined normalised concentration values for populations of women with and without said fetal abnormality.

2. A method according to claim 1 wherein the period between stage A and stage B is between 4 and 8 weeks.

3. A method according to claims 1 wherein the concentration values are normalized by division.

4. A method according to claim 1 wherein the marker is the intact form of hCG.

5. A method according to claim 1 wherein the marker is the beta subunit of hCG.

6. A method according to claim 1 wherein the determination of the concentration of the marker is combined with the determination of the concentration of at least one other marker.

7. A method according to claim 1 wherein the fetal abnormality is Down Syndrome.

8. A method according to claim 1 wherein the fetal abnormality is ectopic pregnancy, open spina bifida, neural tube defects, ventral wall defects, Edwards Syndrome, Pateaus Syndrome, Turner Syndrome, Monosomy X or Kleinfelter's Syndrome.

9. An apparatus comprising means for receiving measurements of levels of a serum marker in a body fluid of a pregnant woman or a precursor or metabolite of said marker, the marker being one where at one stage of gestation (stage A) a mean or median level of the marker differs by less than 20% between pregnancies which are affected and unaffected by a fetal abnormality and at another stage of gestation (stage B) differs by more than 50% between such affected and unaffected pregnancies, there being a period of at least 3 weeks between stage A and stage B, and computer means for comparing the measurements of said levels with each other and to sets of reference data to determine fetal abnormalities, wherein the computer means serves to compare concentrations of the marker for an individual woman made at stage A and at stage B to produce a normalized concentration value and to compare the thus determined normalized concentration value with reference data relating to similarly determined normalized concentration values for populations of women with and without said fetal abnormality.

* * * * *